United States Patent [19]

LeVay et al.

[11] Patent Number: 5,614,151
[45] Date of Patent: Mar. 25, 1997

[54] ELECTRODELESS STERILIZER USING ULTRAVIOLET AND/OR OZONE

[75] Inventors: Thurston C. LeVay, Arcadia; James A. Rummel, Placentia, both of Calif.

[73] Assignee: R Squared Holding, Inc., Santa Ana, Calif.

[21] Appl. No.: 483,078

[22] Filed: Jun. 7, 1995

[51] Int. Cl.⁶ .............................. A61L 2/12; A61L 2/20; C02F 1/32; C02F 1/78
[52] U.S. Cl. .............................. 422/24; 422/23; 422/121; 422/186.3; 313/639; 250/455.11; 250/504 R
[58] Field of Search .............................. 422/24, 121, 23, 422/28, 186.3; 250/455.11, 504 R, 374, 375; 313/639

[56] References Cited

U.S. PATENT DOCUMENTS

| | | | |
|---|---|---|---|
| 3,372,672 | 3/1968 | Wright et al. | 118/724 |
| 3,819,970 | 6/1974 | Roche | 313/573 |
| 3,851,202 | 11/1974 | Troue | 313/636 |
| 3,911,318 | 10/1975 | Spero et al. | 315/39 |
| 4,028,080 | 6/1977 | Di Vita et al. | 65/425 |
| 4,028,135 | 6/1977 | Vig et al. | 134/1 |
| 4,199,419 | 4/1980 | Holroyd et al. | 250/527 X |
| 4,263,702 | 4/1981 | Vig et al. | 29/25.35 |
| 4,342,915 | 8/1982 | Karamian | 250/436 |
| 4,492,898 | 1/1985 | Lapatovich et al. | 315/248 |
| 4,675,577 | 6/1987 | Hanlet | 315/248 |
| 4,812,714 | 3/1989 | Keefe et al. | 315/60 |
| 4,822,450 | 4/1989 | Davis et al. | 156/643.1 |
| 4,957,114 | 9/1990 | Zeng et al. | 128/665 |
| 5,029,252 | 7/1991 | Ameseder | 422/24 X |
| 5,063,030 | 11/1991 | Sweetman | 422/189 |
| 5,166,528 | 11/1992 | Le Vay | 422/24 X |
| 5,173,638 | 12/1992 | Eliasson et al. | 313/634 |
| 5,268,104 | 12/1993 | Masoomain | 210/638 |
| 5,336,969 | 8/1994 | Weiss et al. | 313/580 |
| 5,387,400 | 2/1995 | Pelster | 422/24 X |
| 5,426,308 | 6/1995 | Sudduth et al. | 250/504 H |

FOREIGN PATENT DOCUMENTS

| | | | |
|---|---|---|---|
| 0218244 | 4/1987 | European Pat. Off. | |
| 0277505 | 8/1988 | European Pat. Off. | |
| 0285446 | 10/1988 | European Pat. Off. | |
| 0299244 | 1/1989 | European Pat. Off. | |
| 0490883 | 6/1992 | European Pat. Off. | |
| 507533 | 10/1992 | European Pat. Off. | 313/639 |

Primary Examiner—Robert J. Warden
Assistant Examiner—E. Leigh Dawson
Attorney, Agent, or Firm—Christie, Parker & Hale, LLP

[57] ABSTRACT

A sanitizer uses a radiant energy source such as a microwave source to excite a gas contained in a bulb so that the gas produces ultraviolet radiation that can be used to sanitize substances exposed to the radiation. The ultraviolet radiation may also be used to generate ozone from oxygen in air or another gas containing oxygen and the ozone may be used by itself or in combination with ultraviolet exposure to sanitize substances. The bulb for generating ultraviolet radiation can be shaped so that substances to be sterilized are able to pass through the bulb, so that objects (even metal objects) are enclosed by the bulb and shielded from the radiant energy source, or so that the bulb is located at the end of a waveguide and can be positioned to sanitize inaccessible surfaces or substances.

13 Claims, 4 Drawing Sheets

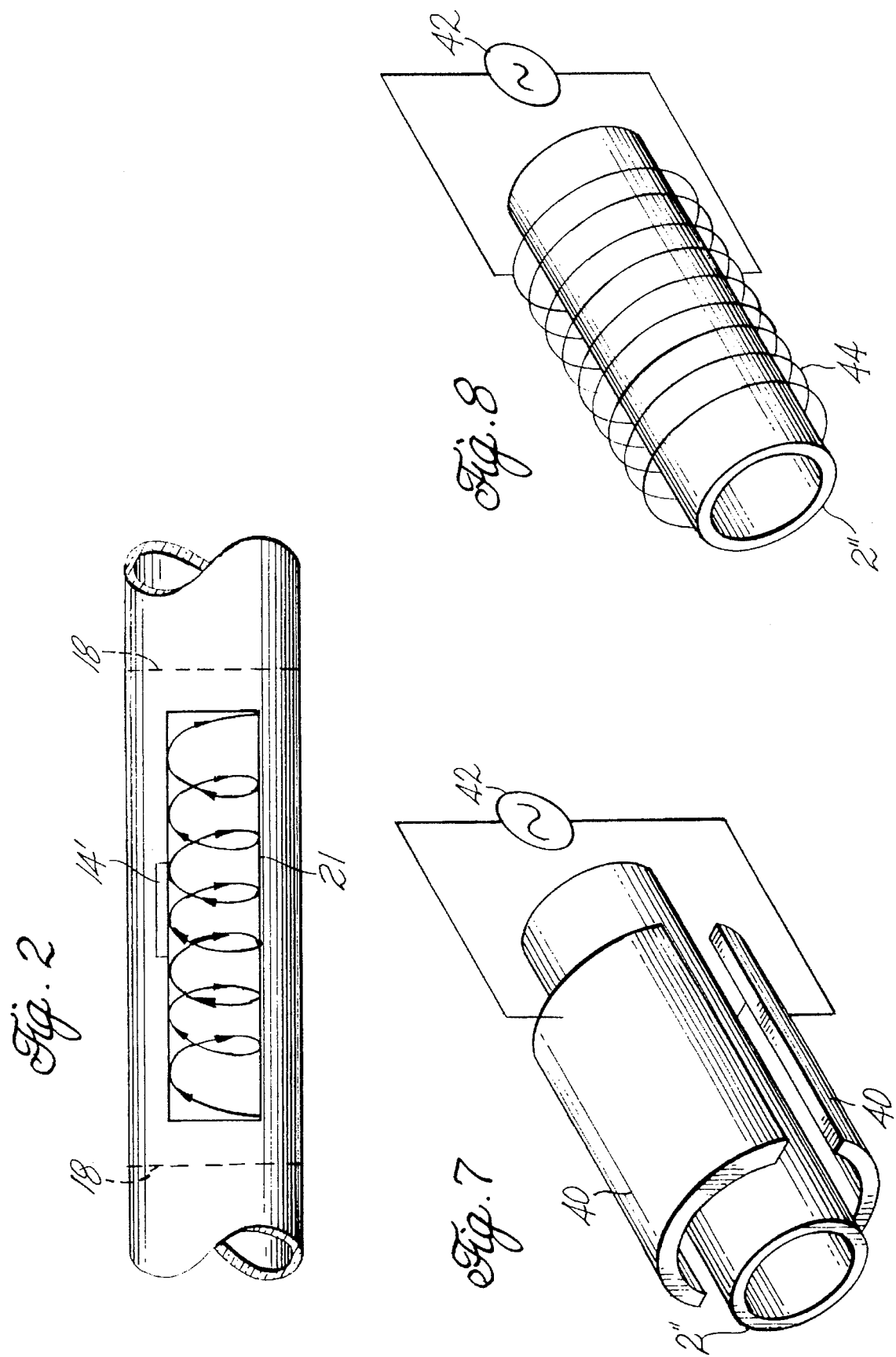

ELECTRODELESS STERILIZER USING ULTRAVIOLET AND/OR OZONE

FIELD OF THE INVENTION

The present invention relate to a sterilizer for sanitizing or disinfecting a substance. More particularly, the invention relates to an ultraviolet sterilizer responsive to a radiant energy source which produces ozone for enhanced sterilization.

BACKGROUND OF THE INVENTION

The surface sterilizing effects of ultraviolet radiation has been described in the patent literature. One of the earlier patents to describe such a phenomenon is in U.S. Pat. No. 2,407,379 where an ultraviolet lamp for surface sterilization and general bactericidal use is disclosed.

The concept of using ultraviolet radiation for surface sterilization is well known. For example, U.S. Pat. No. 4,803,364 describes a toothbrush conditioner which has a housing with an ultraviolet source inside for sterilizing a toothbrush. U.S. Pat. No. 4,448,750 describes a method for disinfecting and/or sterilizing small objects wherein the object to be disinfected or sterilized is vibrated at a frequency range of 8 to 300 KHz while being exposed to an ultraviolet source.

While the above-referenced methods of surface sterilization may find some applications, they are expensive, cumbersome, difficult to use, and have not enjoyed wide commercial success. Moreover, external power sources coupled to the ultraviolet lamp through electrical connectors are typically required.

In an attempt to overcome this problem, U.S. Pat. No. 5,166,528 describes an electrodeless ultraviolet sterilizer device excited by a microwave source. The microwave source is a microwave oven wherein a plurality of bulbs are disposed inside the oven for providing an ultraviolet source. In use, the object to be sterilized is placed in the microwave oven. Power is applied causing the bulbs to emit ultraviolet radiation directed at the object.

Alternative methods to sanitize or disinfect substances have been contemplated. Exemplary is the use of ozone which is increasingly being used in water purification, bleaching, and chemical manufacturing processes where a strong oxidizing agent is needed. Typically, ozone is prepared by a device called an ozonizer, which produces ozone by passing an electric spark through a stream of air containing oxygen. Only a small fraction of the air containing oxygen is converted to ozone by this process. The ozone is directed to the surface of an object to be sterilized where it oxidizes the microorganisms on the surface of the object.

Accordingly, it would be desirable to provide an ultraviolet sterilizer having commercial, industrial, medical and personal applications which simultaneously produces ozone as a byproduct of the sterilization product to achieve a synergistic effect in destroying microorganisms.

SUMMARY OF THE INVENTION

The present invention is directed, in a preferred embodiment, to a synergistic ultraviolet sterilizer that satisfies the need for such a sterilizer. It is also directed to an improved electrodeless sterilizer capable of being used in a broad range of applications. There is, therefore, provided according to a preferred embodiment an ultraviolet sanitizing device having a bulb with an elongated ultraviolet transparent inner surface for passing a substance to be sanitized therethrough and an elongated outer surface formed with said inner surface to define a sealed annular region therebetween for containing a gas. A radiant energy source is located in the proximity of the bulb and directed thereto for exciting the gas contained in the bulb and to thereby produce ultraviolet radiation. Substance is defined herein as any gas, liquid, solid or combination thereof.

An attractive feature of the present invention is that by passing a substance through the center of the ultraviolet bulb, enhanced exposure to the sanitizing ultraviolet radiation and elimination of shadowing is achieved thereby reducing the sterilization time and thus reducing the energy dissipated in the process. This feature is ideal for large commercial applications where energy consumption is of paramount concern.

Another attractive feature of the present invention is that ozone may be produced from the sterilization process itself to produce a synergistic effect. The ultraviolet light used to sterilize the substance may be used to produce ozone to effect a further sterilization of the surface.

The present invention may be used on a variety of substances including metal objects. For sterilization of metal objects, a bulb should be used that substantially encloses the object. The bulb provides attenuation of the microwave field and effectively shields the object.

In an alternative embodiment of the present invention, a radiant energy source may be placed in an enclosure with an ultraviolet source. An input feed is provided for introducing air containing oxygen into the enclosure whereby ozone is produced by exciting the air containing oxygen with ultraviolet radiation. A flexible hose is mounted to the output of the enclosure to distribute the ozone to an external substance for oxidizing microorganisms. Preferably, a nozzle is provided to control the discharge rate of the ozone.

In another alternative embodiment of the present invention, a microwave generator feeds a waveguide which terminates into a small ultraviolet bulb. This embodiment provides a means to sterilize or sanitize areas which are not easily accessible such as internal parts of systems, air ducts and pipings. This embodiment may also be useful in therapeutical applications for medical procedures.

BRIEF DESCRIPTION OF THE DRAWINGS

These and other features, aspects and advantages of the present invention will become better understood with regard to the following description, appended claims, and accompanied drawings where:

FIG. 2 is a perspective view of an ultraviolet sanitizer disposed in an air shaft;

FIG. 7 is a perspective view of an ultraviolet tube excited by a parallel plate configuration; and FIG. 8 is a perspective view of an ultraviolet tube excited by an inductor.

DETAILED DESCRIPTION

Figure 1:
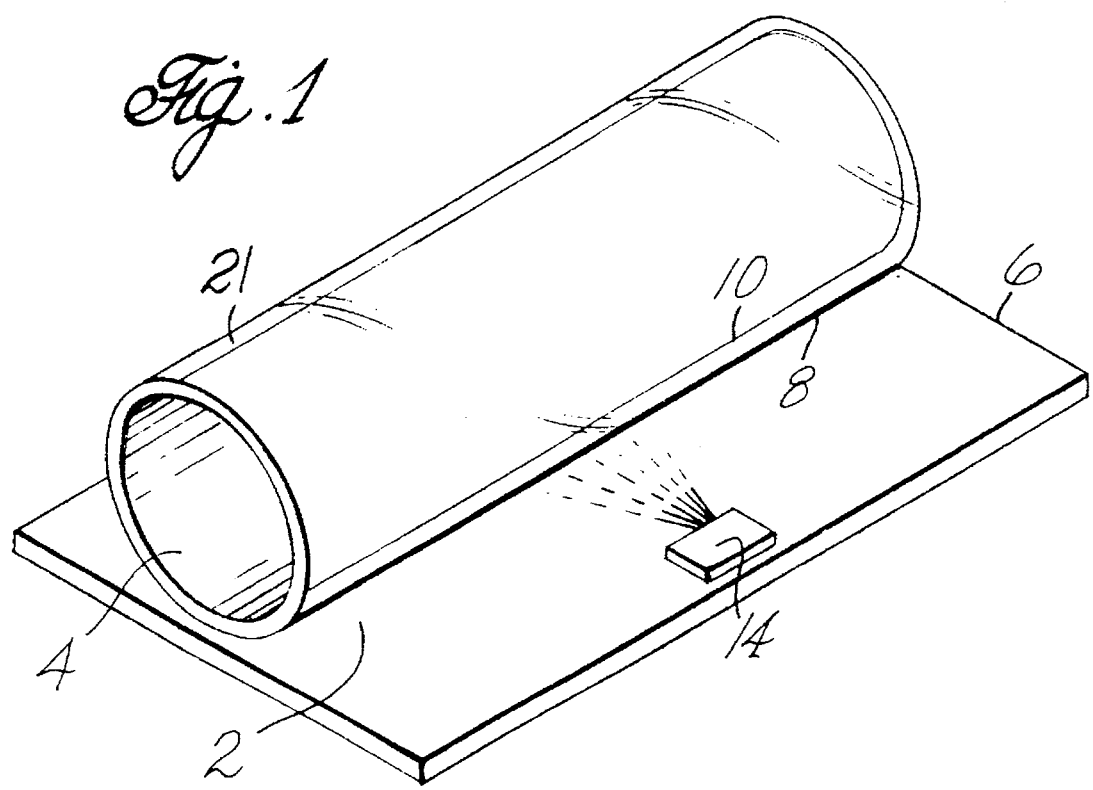
FIG. 1 is a perspective view of an ultraviolet tube sanitizer for sanitizing integrated circuits and other objects.

An ultraviolet sanitization embodiment of the present invention is shown in FIG. 1. A glass tube or bulb 2 having a passageway 4 through its center for receiving a substance to be sanitized is mounted onto a supporting structure 6. The glass tube or bulb is made of an ultraviolet transparent material which is typically quartz. The quartz bulb 2 has a dewar type construction having a double wall 8 and 10, in which a region between the walls 21 is evacuated and sealed at both ends. A small amount of mercury is placed in the evacuated region during manufacture. During lamp operation, the mercury vaporizes to a very low pressure. At this pressure, the current through the vapor caused by the radiant energy source incident thereon causes the vapor to radiate energy most strongly at one specific wavelength in the ultraviolet region (253.7 nanometers). A small quantity of filling gas may also be placed in the evacuated region to aid starting in operation. Argon and argon-neon are the most common, but occasionally krypton is used. The filling gases ionize readily when exposed to the radiant energy source. The ionized filling gas quickly decreases the resistance allowing current to flow and the mercury to vaporize.

To enhance the ionization process, it is particularly useful to place a conductor or semiconductor such as a piece of nichrome or tungsten wire (not shown) inside the tube. The wire should be small, e.g., in the range of 0.001 to 0.005 inch diameter and about 1 to 2 inches long, to avoid appreciable heat production in response to the radiant energy source. The wire acts like an antenna and facilitates the breakdown or ionization of gas within the quartz bulb and the emission of ultraviolet light.

A magnetron 14 is an exemplary radiant energy source. As shown in FIG. 1 the magnetron is mounted onto the supporting structure 6 and directed to the glass or tube 2. When the magnetron is excited, external radiation falls incident on the quartz bulb 2. This radiation causes the initial ionization of the filling gas which ultimately facilitates the vaporization of mercury.

Alternatively, the radiant energy source may comprise a radio frequency electromagnetic oscillator for exciting the mercury disposed in the quartz tube 2 by a pair of opposed plates 40 as shown in FIG. 7 or a coil 44 as shown in FIG. 8.

In operation, a substance such as an integrated circuit may be inserted into the passageway 4 of the quartz bulb 2. The magnetron emits microwave energy which causes the vaporized mercury disposed within the quartz bulb 2 to release wavelengths of ultraviolet energy directed to the substance inside the passageway. In this configuration, the outer wall 8 of the glass tube 2 must be microwave transparent to couple the radiant energy to the mercury. Similarly, the inner wall 10 must be ultraviolet transparent so that the ultraviolet radiation falls incident upon the substance to be sanitized. This embodiment further has commercial applications wherein a plurality of integrated circuits or other substances can be fed continuously through the ultraviolet passageway such as on a conveyor belt at a rate sufficient to insure that the substance is sanitized.

Typically sterilization is achieved in a relatively short time. The sterilization time depends on a number of factors, such as the diameter of the passageway, the intensity of the ultraviolet radiation, and the microorganisms to be destroyed.

Further sterilization may be achieved by introducing air containing oxygen into the ultraviolet field to produce ozone for oxidizing the microorganisms contained in or on the substance as it passes through the quartz bulb 2. This produces a synergetic effect as further sterilization of the substance is effected.

Turning to FIG. 2, the ozone producing effects of the present invention has immediate application for sanitizing air in an air duct. In this embodiment, the quartz bulb 2' is disposed in an air duct 16 for receiving a continuous air stream containing oxygen. The quartz bulb is excited by a microwave source 14' located in close proximity thereto. As the air passes through the air duct, the ultraviolet radiation falls incident thereon to produce ozone from the oxygen in the air. The ozone acts to oxidize microorganisms contained in the air flow internal to the air duct 16. The air duct 16 should be coated with a material that is ultraviolet reflective to minimize the losses. Preferably, microwave shielding 18 should be placed at the input and output of the passageway of the quartz tube 2'.

Figure 3:
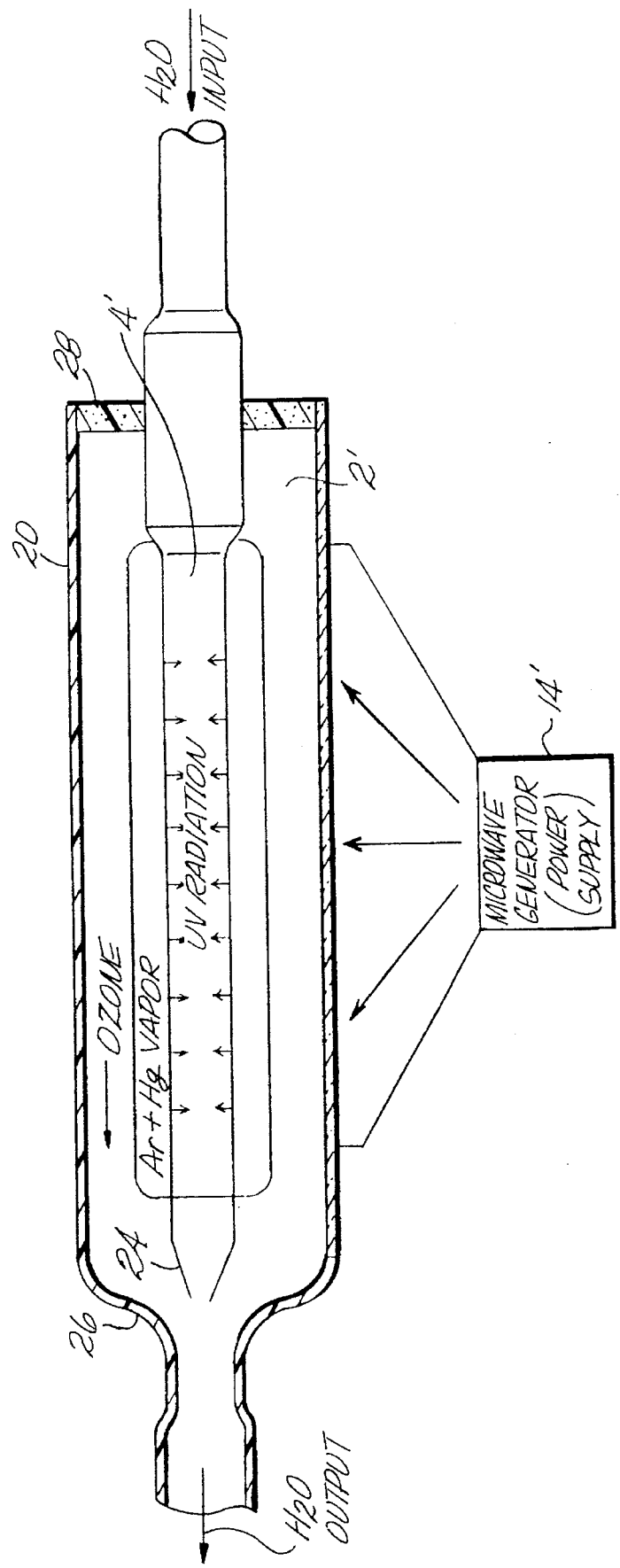
FIG. 3 is an ultraviolet sanitizer used in a water sanitizing system.

The use of ozone to enhance the sanitization of a liquid substance in conjunction with ultraviolet radiation is best shown in FIG. 3. In this embodiment, the ultraviolet sterilization device can be inserted in the path of a water inlet for purification purposes. Referring to FIG. 3, an enclosure is provided which is formed around the periphery of the quartz bulb 2' for receiving air containing oxygen therethrough. The quartz bulb 2' is formed with an extension at its inlet which extends beyond the end of the enclosure 20 for receiving a steady flow of water to be sanitized. The water is passed through the inner passageway 4' of the quartz tube 2' where it is subjected to ultraviolet radiation which in turn destroys microorganisms contained in the water.

The quartz tube 2' is further formed with an outlet orifice 24 downstream from the output to form an aspirator. Oxygen or air containing oxygen is drawn into the region defined by the outer surface of the quartz bulb 2' and the enclosure where it is acted upon by the ultraviolet radiation resulting in the production of ozone. In this embodiment, the quartz bulb 2' must have an ultraviolet transparent outer surface for producing an ultraviolet field across the air containing oxygen for producing ozone. The quantity of ozone produced can be controlled by properly doping the quartz bulb by a process well known in the art. The enclosure is formed with a neck 26 downstream from the air containing oxygen for drawing the ozone into the water to effect a further sanitization thereof. Preferably, a dust filter 28 should be inserted in line with the air containing oxygen flow at the input of the enclosure. A radiant energy source, such as a microwave generator 14' may be used to excite the quartz bulb 2' In this configuration, a feed may be utilized to couple the microwave energy to the enclosure 20. The enclosure must be microwave transparent at the point of incidence of the microwave field. Alternatively the enclosure may be provided with an aperture for coupling the microwave energy into the enclosure.

Figure 4:
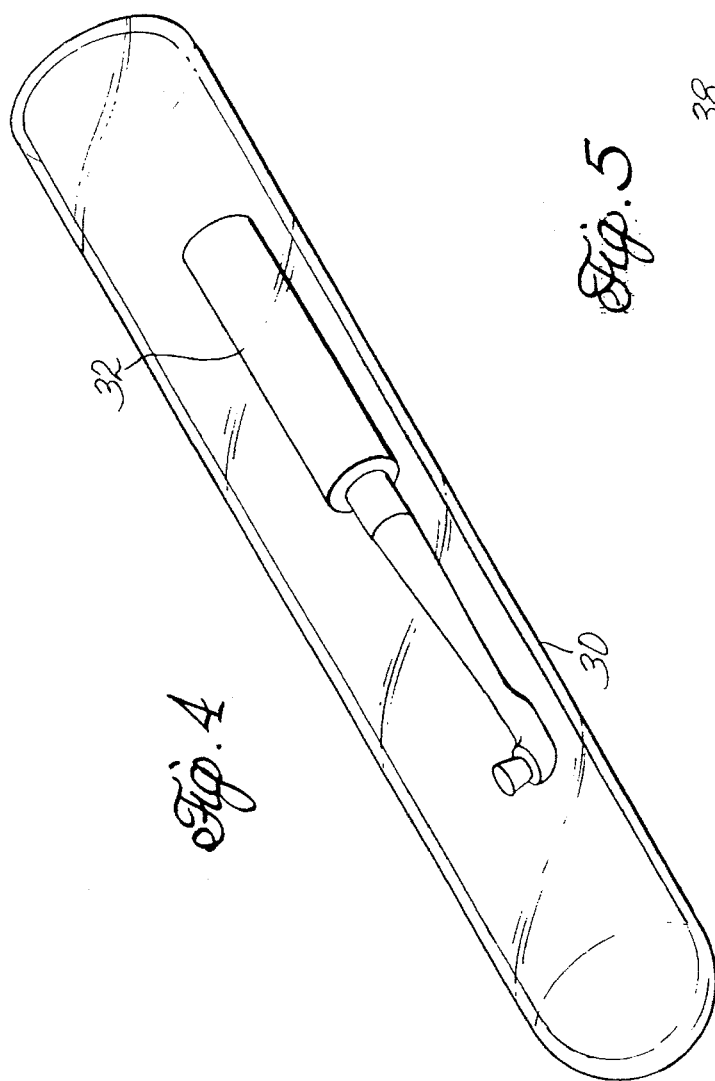
FIG. 4 is an ultraviolet sanitizer designed for dental hand pieces and other small instruments.

Turning to FIG. 4, a dewar type construction quartz bulb is used for sanitizing small articles such as dental pieces and the like. The construction of the ultraviolet bulb 30 is similar to that described in FIGS. 1–3 except that one end of the passageway is sealed to hold a small article 32. The ultraviolet bulb 30 along with the article 32 is placed in a radiant energy field whereby the mercury contained in the quartz bulb 2' is vaporized to emit ultraviolet radiation incident on the article 32 for destroying microorganisms. Additionally, the air containing oxygen surrounding the device may be excited by the ultraviolet radiation causing ozone to be produced for oxidizing the microorganisms contained on the surface of the article 32 as described above. Preferably, the quartz bulb 2' should be tilted at an angle downward toward its closed end during operation so that a concentration of ozone is formed at the bottom of the quartz bulb adjacent to the object to be sterilized to effect further sterilization. The tilting of the quartz bulb 2' may be performed by a mechanical apparatus or any other means known in the art. The bulb could also be held horizontal for loading and tilted upward at the closed end for unloading of the object to be sterilized. In addition, in a case where the article is a metal object, the quartz bulb 30 attenuates the radiant energy source which falls incident on the article 32. This attenuation allows the metal article to be sanitized in a microwave enclosure by merely enclosing said article in the quartz bulb.

Figure 6:
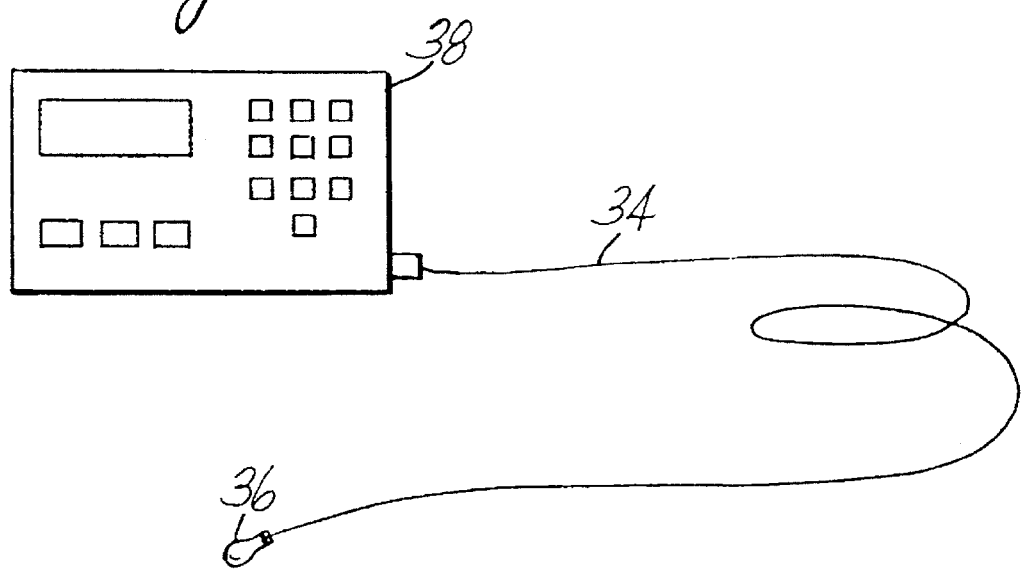
FIG. 6 is a perspective view of an ultraviolet pipe used to sanitize internal parts that are difficult to access.

Referring to FIG. 6, an ultraviolet light pipe is depicted wherein the microwave energy is directed to a small ultraviolet bulb 36 by a flexible waveguide 34. In this embodiment the microwave energy is produced by a microwave generator 38 such as a magnetron or cyclotron. The vaporization of the mercury contained in the quartz bulb is initiated by the microwave energy delivered to it by the flexible waveguide. Alternatively, an optic feed may be used to transmit the ultraviolet radiation from a bulb located at the microwave generator to the point of sterilization or a microwave source may be located at the end of a flexible arm and adjacent an ultraviolet bulb. This application is used for sterilizing surfaces of internal parts that are not readily accessible such as internal parts of systems, air ducts and pipings.

Figure 5:
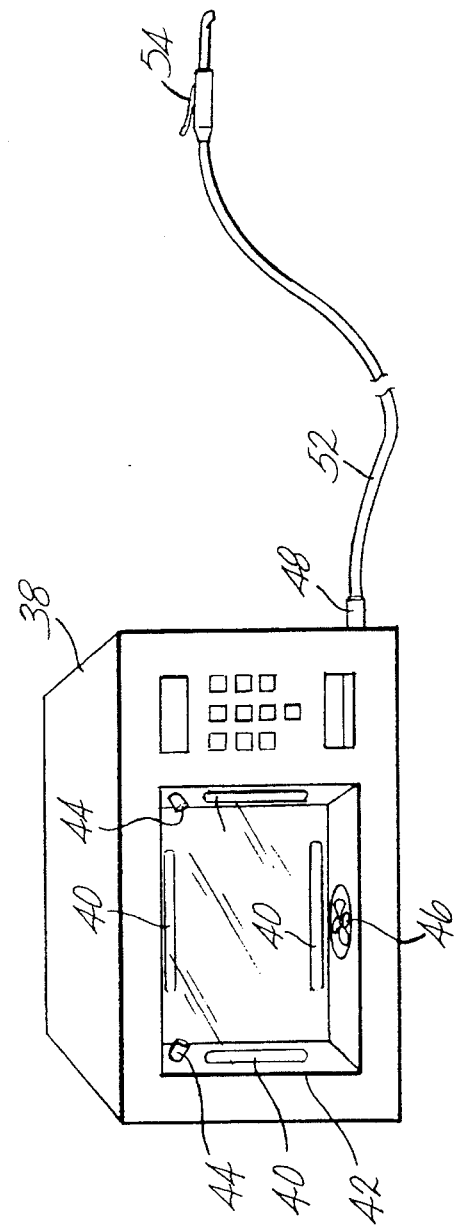
FIG. 5 is a perspective view of an ozone generator used to sanitize external objects.

FIG. 5 depicts an ozone generator for delivering ozone to an external substance for oxidation of microorganisms in or on the surface of a substance. A plurality of quartz bulbs 40 is disposed within the ozone generator in an ozone chamber 42. A feed 44 is provided to deliver air containing oxygen from the atmosphere to the ozone chamber 42. As described above in detail, the ultraviolet radiation incident upon the air containing oxygen produces ozone within the ozone chamber. A plurality of exhaust fans 46 are provided to direct the ozone to an output connector 48. A flexible hose 52 having a mating connector 50 is detachably mounting to the external connector of the ozone generator 48. A nozzle 54 is connected to the other end of the flexible hosing 52 to control the discharge of ozone onto a substance to be sterilized.

It is apparent from the foregoing that the present invention satisfies an immediate need for an ultraviolet sanitization system using the principles of oxidation to further enhance the sanitization process for commercial applications. The present invention satisfies this need by providing a feed through ultraviolet generating source in the presence of air containing oxygen. This ultraviolet sanitization system may be embodies in other specific forms and used with a variety of lighting devices without departing from the spirit or essential attributes of the present invention. It is therefore, desired that the present embodiment be considered in all respects as illustrative and not restrictive, reference being made to the appended claims rather than the foregoing description to indicate the scope of the invention.

What is claimed is:

1. An ultraviolet sanitizing device comprising:
   an ultraviolet transparent bulb having an elongated inner surface extending around a central axis to form a passage having an inlet and an outlet, and an elongated outer surface formed with said inner surface to define a sealed region therebetween, said sealed region being filled with a gas;
   a radiant energy source directed at said bulb for ionizing the gas in the sealed region to produce ultraviolet radiation;
   means for receiving an oxygen containing gas external to the bulb, the ultraviolet radiation acting upon the oxygen containing gas external to the bulb to produce ozone, said ozone having a first pressure; and
   means for creating a second pressure at the outlet of the passage, said second pressure being lower than said first pressure so that the ozone is drawn toward the outlet of the passage.

2. The ultraviolet sanitizing device of claim 1 further comprising a wire disposed in said sealed region of said bulb for initiating the ionization process of the gas.

3. The ultraviolet sanitizing device of claim 1 wherein said inner and outer surfaces of the bulb are cylindrical.

4. The ultraviolet sanitizing device of claim 1 wherein the means for creating a second pressure comprises a tapered orifice at the outlet of the passage.

5. The ultraviolet sanitizer device of claim 4 wherein the means for receiving ozone comprises an enclosure formed around the bulb.

6. The ultraviolet sanitizing device of claim 5 wherein said radiant energy source comprises a microwave source.

7. The ultraviolet sanitizing device of claim 6 wherein at least a portion of said enclosure is microwave transparent.

8. The ultraviolet sanitizing device of claim 7 further comprising a feed for coupling microwaves emitted by said microwave source to said enclosure.

9. The ultraviolet sanitizing device of claim 5 wherein said enclosure is formed with a neck adjacent to said orifice for facilitating the drawing of the ozone toward the first end of the passage.

10. The ultraviolet sanitizing device of claim 1 wherein said radiant energy source comprises a radio frequency oscillator.

11. A method of sanitizing a substance using ultraviolet radiation emitted from a bulb, comprising the steps of:
   providing a bulb comprising an elongated inner surface extending around a central axis to form a passage through which a substance to be sanitized passes, and an elongated outer surface formed with the inner surface to define a sealed region therebetween, said sealed region being filled with a gas;
   ionizing the gas to emit ultraviolet radiation;
   passing a substance to be treated through the passage so that the substance is exposed to the ultraviolet radiation;
   receiving an oxygen containing gas external to the bulb;
   exposing said oxygen containing gas external to the bulb to said ultraviolet radiation to produce ozone, said ozone having a first pressure;
   creating a second pressure at the outlet of the passage, said second pressure being lower than said first pressure so that the ozone is drawn toward the outlet of the passage, thereby sanitizing a substance passing through the outlet.

12. The method of sanitizing a substance of claim 11 wherein the step of creating a second pressure is performed by passing the substance through a tapered orifice at the outlet of the passage.

13. The method of sanitizing a substance of claim 12 wherein the step of receiving the ozone comprises forming an enclosure around the bulb.

* * * * *

UNITED STATES PATENT AND TRADEMARK OFFICE
CERTIFICATE OF CORRECTION

PATENT NO. : 5,614,151
DATED : March 25, 1997
INVENTOR(S) : Thurston C. LeVay and James A. Rummel It is certified that error appears in the above-indentified patent and that said Letters Patent is hereby corrected as shown below:

Column 1, line 26, change "KHz" to -- kHz --.
Column 2, lines 48, 49, change "accompanied" to -- accompanying --.

Column 4, line 48, after "bulb 2'" insert a period.
Column 5, line 37, change "mounting" to -- mounted --.
Column 5, line 49, change "embodies" to -- embodied --.
Column 5, line 52, change "It is therefore," to -- It is, therefore, --.

Signed and Sealed this

Tenth Day of February, 1998

Attest:

BRUCE LEHMAN

*Attesting Officer*  *Commissioner of Patents and Trademarks*